(12) United States Patent
Lange

(10) Patent No.: US 7,352,456 B2
(45) Date of Patent: Apr. 1, 2008

(54) METHOD AND APPARATUS FOR INSPECTING A SUBSTRATE USING A PLURALITY OF INSPECTION WAVELENGTH REGIMES

(75) Inventor: Steven R. Lange, Alamo, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 111 days.

(21) Appl. No.: 10/410,126

(22) Filed: Apr. 8, 2003

(65) Prior Publication Data

US 2004/0201837 A1 Oct. 14, 2004

(51) Int. Cl.
*G01N 21/00* (2006.01)
(52) U.S. Cl. .................. 356/237.2; 356/237.5
(58) Field of Classification Search .. 356/237.1–237.5, 356/239.1, 239.2, 446
See application file for complete search history.

(56) References Cited

U.S. PATENT DOCUMENTS

| 4,498,772 | A | | 2/1985 | Jastrzebski et al. | |
|---|---|---|---|---|---|
| 4,877,326 | A | * | 10/1989 | Chadwick et al. | 356/394 |
| 5,179,422 | A | * | 1/1993 | Peterson | 356/237.1 |
| 5,293,538 | A | | 3/1994 | Iwata et al. | |
| 5,825,498 | A | | 10/1998 | Nuttall et al. | |
| 5,936,726 | A | * | 8/1999 | Takeda et al. | 356/237.2 |
| 6,157,444 | A | * | 12/2000 | Tomita et al. | 356/237.1 |
| 6,266,137 | B1 | | 7/2001 | Morinaga | |
| 6,392,793 | B1 | | 5/2002 | Chuang et al. | |
| 2003/0008448 | A1 | | 1/2003 | Kafka et al. | |
| 2005/0052643 | A1 | * | 3/2005 | Lange et al. | 356/237.1 |

FOREIGN PATENT DOCUMENTS

| WO | 01/40145 | 6/2001 |
|---|---|---|
| WO | 02/25708 | 3/2002 |

OTHER PUBLICATIONS

Patent Abstracts of Japan, publication No. 04026845, published Jan. 1992.
International Search Report, PCT/US2004/010324, mailed Sep. 10, 2004.

* cited by examiner

*Primary Examiner*—Hoa Q. Pham
(74) *Attorney, Agent, or Firm*—Baker & McKenzie LLP (57) ABSTRACT

A surface inspection apparatus and method are disclosed. In particular, the method and apparatus are capable of inspecting a surface in two (or more) optical regimes thereby enhancing the defect detection properties of such method and apparatus. A method involves illuminating the surface with light in a first wavelength range and a second wavelength range. The first wavelength range selected so that the surface is opaque to the light of the first wavelength range so that a resultant optical signal is produced that is predominated by diffractive and scattering properties of the surface. The second wavelength range is selected so that the surface is at least partially transmissive to light in the second wavelength range so that another resultant optical signal is produced that is predominated by thin film optical properties of the surface. The resultant optical signals are detected and processed to detect defects in the surface. Devices for implementing such methods are also disclosed.

28 Claims, 8 Drawing Sheets

Fig. 1

Related Art

METHOD AND APPARATUS FOR INSPECTING A SUBSTRATE USING A PLURALITY OF INSPECTION WAVELENGTH REGIMES

TECHNICAL FIELD

The invention described herein relates generally to tools and methods used for conducting surface inspections. In particular, the invention relates to methods and apparatus for inspecting a substrate using two or more inspection modes to achieve enhanced defect detection during inspection. Such inspections can be used to inspect substrates including, but are not limited to, semiconductor substrates and photomasks.

BACKGROUND

For many years, various brightfield, darkfield, and e-beam scanning methodologies have been used to inspect surfaces. These scanning technologies make use of radiation scattered, diffracted, and/or reflected by a surface to characterize and examine features of the surface. In particular, such scanning technologies are used to examine surfaces to determine the presence and location of defects in an inspected surface. The details of these and other related scanning and inspection technologies are well known to those having ordinary skill in the art.

Typically, such devices examine a surface by projecting a light beam onto the surface and then detecting resulting pattern of light received from the surface. Also typically, light beams are projected onto the surface over a single frequency (e.g., as typified by laser devices) or over a bandwidth of frequencies (such as can be obtained using appropriately filtered arc lamps).

In an effort to identify defects of ever decreasing sizes, conventional tools typically rely on illumination sources having shorter and shorter wavelengths. As is well-known to those having ordinary skill in the art, illumination of a surface with shorter wavelengths of light can be used to obtain greater resolution in images of the surface. Previously, greater resolution has been thought to be the key to improving defect detection of smaller defects. The inventor has discovered that greater resolution is only part of the defect identification story.

Figure 1:
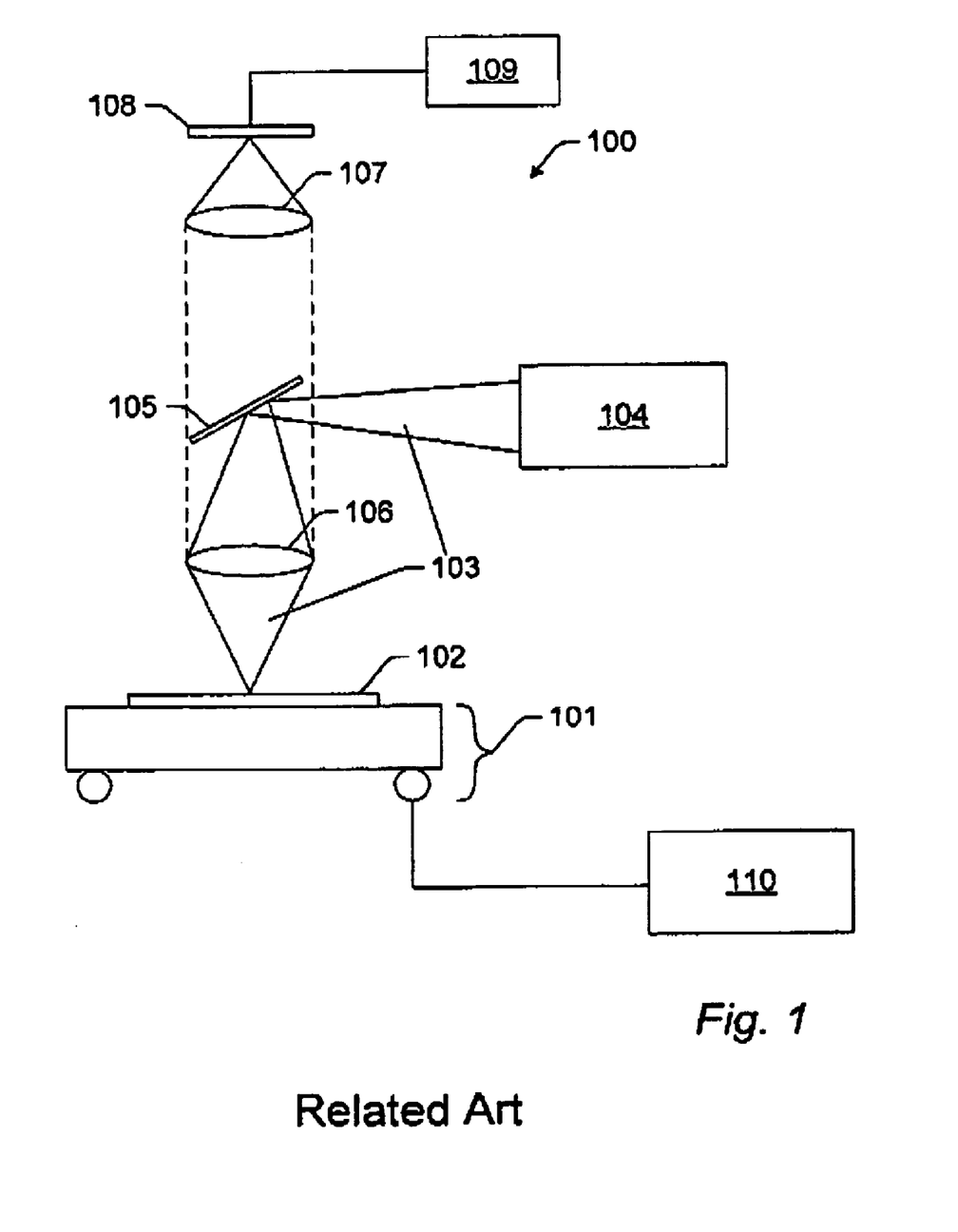
FIG. 1 depicts a conventional bright field surface inspection tool of a type known in the art.

A common implementation of a conventional inspection tool is shown by the simplified schematic representation of a bright field inspection tool 100 shown in FIG. 1. An object 102 (commonly, a wafer) is secured to a movable stage 101 where it is illuminated by a light beam 103 produced by a single light source 104. Commonly, the light source 104 comprises a single arc lamp selectively filtered to produce a defined bandwidth of frequencies. In some alternatives, the light source 104 comprises a laser tuned to produce a single frequency coherent beam of light centered at some peak wavelength. Commonly, the light beam 103 is directed onto a partially transmissive surface 105 that reflects a portion of the light beam 103 through an objective lens system 106 which directs the beam 103 on the surface 102. Typically, different portions of the object 102 are successively inspected by scanning the substrate. Commonly, the stage mounted object 102 is scanned by moving the stage 101 as directed by a scanning control element 110. As the surface 102 is scanned, light reflected, scattered, diffracted, or otherwise received from the surface 102 passes through the objective 106 and passes back through the partially transmissive surface 105 into an optical system 107 that optimizes the light for detection with a detector system 108. Commonly, such optimization includes magnification, focusing, as well as other optical processing. The detector 108 receives the light and generates an associated electrical signal which is received by image processing circuitry 109. The processing circuitry conducts defect analysis to locate defects in the object 102.

Conventional approaches to detecting defects and process variations in layers of a semiconductor substrate have operated under the assumption that greater resolution in an inspection tool translates into greater sensitivity to the presence of defects. The resolving power of optical inspection tools can be characterized by the "point-spread-function" (PSF) of the tool. The PSF is affected by a number of factors including, but not limited to the optical quality of the lenses (or other optical elements) used in the focusing elements, the wavelength of light, numerical aperture (NA) of the objective lens system, pupil shape, as well as other factors. In general, the resolution of a system is related to the wavelength ($\lambda$) of the exposure source divided by the numerical aperture (NA) of the objective lens system. Therefore, shorter wavelengths can be used to produce greater resolution.

Thus, the prior art the emphasis has generally been on generating inspection tools that use shorter wavelength inspection sources to obtain better resolution, and presumably better sensitivity to defects. Light sources operating at visible wavelengths and near ultraviolet wavelength (e.g., from about 400 nm to about 300 nm) have long been used as illumination sources. For example, mercury (Hg) or mercury xenon (Hg Xe) arc lamps have been used as illumination sources in the near ultra-violet (UV) and visible ranges. But, in the continuing drive for greater resolution, shorter wavelength illumination is desirable. Because the power of Hg and HgXe sources drops off rather dramatically, below 300 nanometers (nm) they are not excellent sources of deep UV (e.g., wavelengths below about 300 nm) illumination. Deep UV (DUV) lasers are a commonly used illumination source in the DUV range. Due to the rather high cost of such sources (especially, the laser sources), no known inspection tools or methods have implemented two (or more) sources to inspect surfaces. In fact, until now there was no reason to attempt to do so. The conventional approach has generally been to devise the shortest wavelength system and implement such a system to obtain the best possible resolution.

Although existing inspection machines and processes accomplish their designed purposes reasonably well, they have some limitations. There is a need for greater sensitivity than is currently provided by existing machines and processes. For these and other reasons, improved surface inspection tools and methodologies are needed.

SUMMARY OF THE INVENTION

In accordance with the principles of the present invention, an apparatus and method for inspecting a surface are disclosed. In particular, the method and apparatus are capable of inspecting a surface in two (or more) optical regimes thereby enhancing the defect detection properties of such method and apparatus.

In one embodiment, the invention describes a method for inspecting a substrate surface. The method involves providing a substrate characterized by an opacity transition wavelength. A first optimal inspection wavelength band is determined. The first optimal inspection wavelength is selected from the wavelengths in the opaque regime defined by wavelengths shorter than the opacity transition wavelength of the substrate. A second optimal inspection wavelength band is determined. The second optimal inspection wavelength band is selected from the wavelengths in the transmissive regime defined by wavelengths longer than the opacity transition wavelength of the substrate. The substrate is illuminated with selected wavelengths of light that include at least one of the first optimal inspection wavelength band, the second optimal inspection wavelength band, or both the first optimal inspection wavelength band and the second optimal inspection wavelength band. The resulting optical signals are detected and used to generate associated electronic signals that are processed to detect defects and process variations in the surface.

In another embodiment, the invention comprises a surface inspection method involving illuminating the surface in two optical regimes. The method involves illuminating the surface with light in at least one of a first wavelength range and a second wavelength range. The first wavelength range is selected so that the surface is opaque to the light of the first wavelength range. The second wavelength range is selected so that the surface is at least partially transmissive to light in the second wavelength range. The resultant optical signals and detected and used to generate an associated electronic signal that is processed to detect defects and process variations in the surface.

Another embodiment of the invention includes an apparatus for detecting defects in an inspected surface. The embodiment includes an illumination element capable of providing illumination in at least two light modes. The first mode of operation of the illumination element provides first wavelengths of light, selected for inspection of the surface in an optical regime where the surface is opaque to said first wavelengths of light. The light of the first mode produces a resultant optical signal that is predominated by diffractive and scattering properties of the surface. The also includes a second mode of operation that provides wavelengths of light in a second optical regime where the surface is at least partially transmissive to said second wavelength of light, thereby producing a resultant optical signal that is predominated by thin film optical properties of the surface. The apparatus is configured to inspect the surface using light in the first mode or in the second mode or in both modes simultaneously. The apparatus further includes a scanning element that enables the apparatus to scan the desired portions inspected surface and an optical system for receiving the resultant optical signal from the inspected surface and producing an associated electronic signal. The apparatus also includes electronic circuitry for processing the electronic signal. Such processing can be used for identifying defects and process variations in the surface.

These and other aspects of the present invention are described in greater detail in the detailed description of the drawings set forth hereinbelow.

BRIEF DESCRIPTION OF THE DRAWINGS

The following detailed description can be more readily understood in conjunction with the accompanying drawings, in which.

It is to be understood that, in the drawings, like reference numerals designate like structural elements. Also, it is understood that the depictions in the Figures are not necessarily to scale.

DETAILED DESCRIPTION OF THE DRAWINGS

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

The inventor has discovered that increasing resolution in an inspection tool does not necessarily correlate to increased sensitivity to defects. In fact illuminated substrates demonstrate a number of heretofore unappreciated optical properties which can be advantageously exploited by embodiments of the invention in order to achieve high signal-to-noise ratios and increased sensitivity to defects. The inventor has discovered that illuminating an object with more than one frequency of light can actually yield better defect detection results that simply employing the highest resolution system. Semiconductor substrates, being constructed of many layers of different materials demonstrate a complex array of optical properties which have made the detection of defects in the substrates a difficult process.

However, the inventor has discovered methods of exploiting these differing material properties to increase the sensitivity of defect detection. As used herein, the term "surface" is intended to encompass the upper portions of a substrate including the several uppermost layers and related structures formed thereon as well as the surface itself. Such surfaces are composed of many layers of material (e.g., Si, SiGe, $SiO_2$, polysilicon, Ti, TiN, Ta, TaN, SiN, low-K dielectric materials, and many, many, other materials). Semiconductor surfaces demonstrate a number of optical properties that can enhance an inspection tools ability to detect defects. Among the optical properties exhibited by substrate surfaces are the propensity of the surface to scatter light, the propensity of the surface to diffract light, and thin film optical properties exhibited by the surface. Moreover, all of these effects have wavelength dependent properties associated with them. Thus, as is the case with semiconductor substrates (and phase-shift masks) when a number of materials are used in many layers of varying thickness dimensions, their combined effects are complex and difficult to predict. However, the inventor has found a way to exploit these varied optical characteristics to enhance defect detection in a substrate surface. This will be discussed in greater detail herein below.

Figure 2:
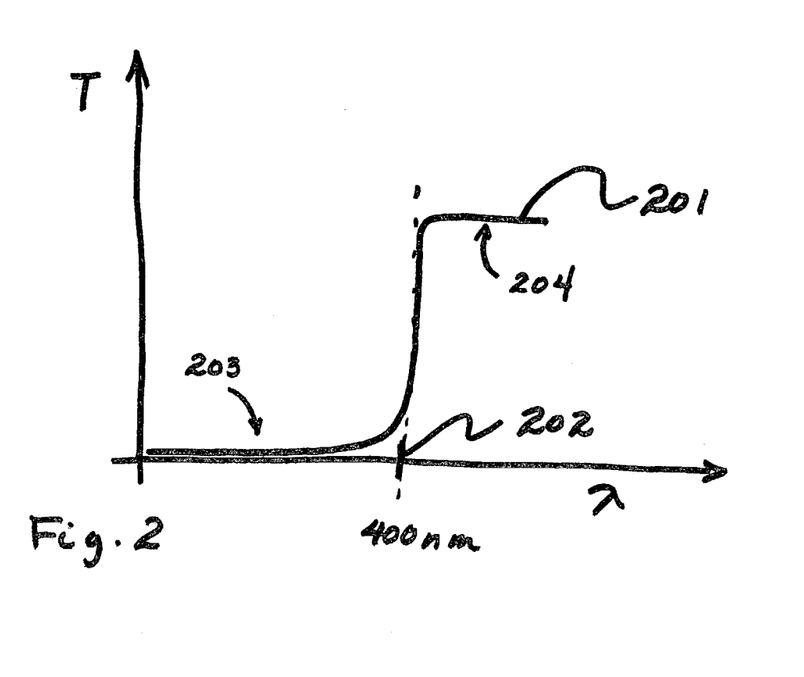
FIG. 2 is a simplified graphical representation of a transmission spectrum for a substrate including a depiction of an opacity transition wavelength for the substrate.

Many materials are used in the construction of semiconductor substrates. Particularly common materials include polysilicon and $SiO_2$. FIG. 2 graphically depicts the transmission spectrum 201 of a thin layer of polysilicon plotted as a function of wavelength ($\lambda$). A characteristic property of polysilicon is the opacity transition wavelength 202 around 400 nm (nanometers). As polysilicon is illuminated with relatively long wavelengths of light (i.e., wavelengths above transition wavelength 202) it behaves as a relatively transmissive material. However, when exposed to shorter wavelengths of light (i.e., wavelengths below the transition wavelength 202), polysilicon changes from a relatively transmissive material (i.e., in region 204) to a relatively opaque material (i.e., in region 203 where relatively little or no light is transmitted).

Figure 3A:
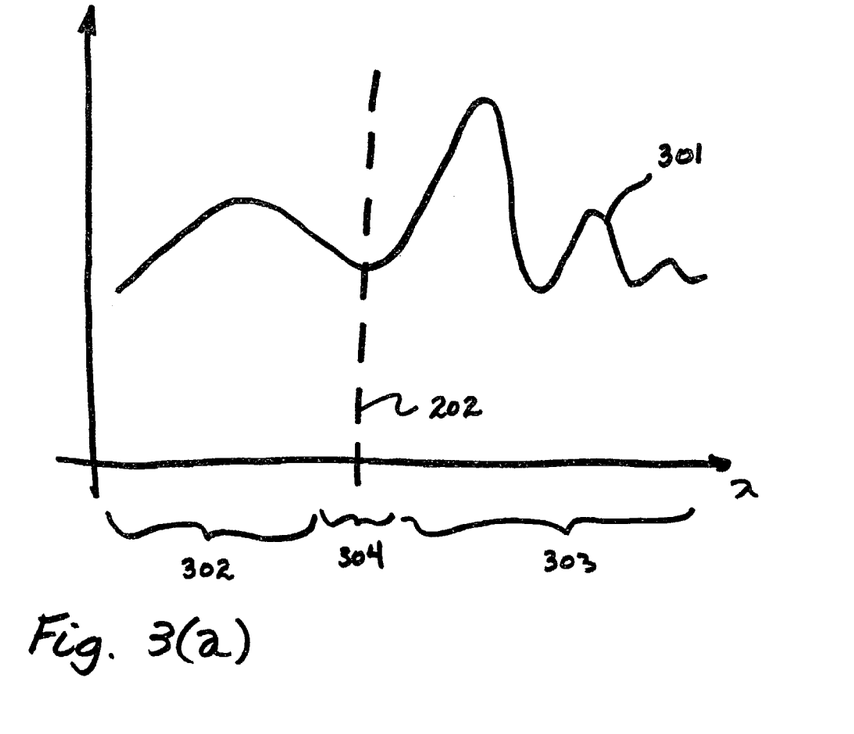
FIG. 3(a) is a simplified graphical depiction of a defect signal showing an opaque regime and a transmission regime.

An example of how such material properties can affect defect detection is illustrated with respect to FIG. 3(a). FIG. 3(a) is a graphical depiction of a "defect signal" produced by a defect associated with polysilicon structures (e.g., layers) on a typical semiconductor substrate. In the depicted figure, the defect signal intensity is plotted as a function of illumination wavelength. When a portion of a surface is illuminated it produces a resultant optical signal (e.g., an image) that can be measured using a detector (e.g., a photodetector). A "defect signal" can be obtained by measuring the resultant optical signal for a portion of a surface containing a defect and comparing it to a resultant optical signal generated by a modeling program (or other suitable non-defect baseline) for the same portion of the surface. By subtracting out the defect-containing signal from the non-defect signal, a "defect signal" can be obtained.

The depicted example of FIG. 3(a) shows a defect signal 301 with signal intensity I plotted as a function of illumination wavelength ($\lambda$). The inventor has discovered that there appear to be two principle mechanisms for producing the defect signals. One mechanism is the diffraction and scattering from opaque surfaces. Another mechanism is the so-called thin film optical effects (e.g., thin film interference effects) caused by the transmissive and partially transmissive films and structures forming the surface. These can be characterized as operating in two different optical regimes. The signal properties of these two different regimes are dramatically different and can be advantageously exploited to improve the sensitivity of inspection tools. In FIG. 3(a) a first regime 302 (also referred to herein as an opaque regime) and a second regime 303 (also referred to herein as a transmissive regime) are depicted. The opaque regime 302 defines a range of wavelengths that are shorter than the opacity transition wavelength 202. Light received from a surface illuminated by wavelengths of light in the opaque regime 302 demonstrates the anticipated ordinary diffraction and scattering properties expected when an opaque material is illuminated. For example, in the opaque regime 302, as the illumination wavelength decreases system resolution tends to increase.

In contrast, when the illumination wavelength ($\lambda$) is increased past a certain point, the light transmission behavior of the substrate changes. For purposes of this patent, wavelengths of light in this regime are said to belong to the transmissive regime. The transmissive regime 303 defines a range of wavelengths that are longer than the opacity transition wavelength 202. Light received from a surface illuminated by wavelengths of light in the transmissive regime 303 exhibits thin film optical properties as the predominant signal producing mechanism. In particular, at such longer wavelengths, the defect signal becomes largely dominated by optical interference properties induced by thin film structures on the substrate. As stated, these interference properties become the predominant mechanism producing the defect signal. At the opacity transition wavelength 202 many materials (especially thin films of such materials) experience this change in light transmission behavior.

Figure 3B:
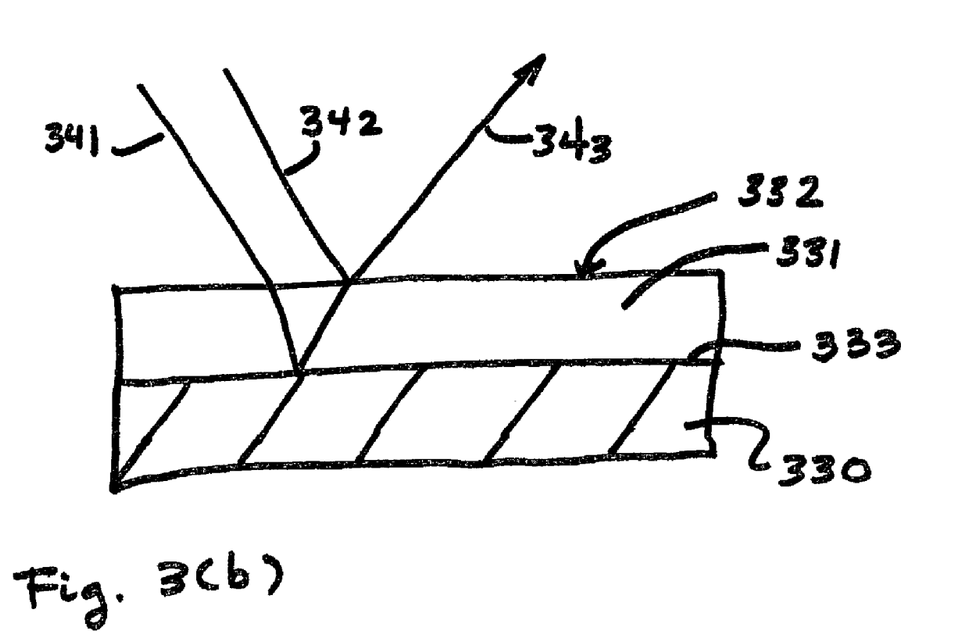
FIG. 3(b) is a simplified diagrammatic representation of a substrate used to illustrate aspects of thin film interference effects.

In order to obtain a more clear understanding of the previously described "transmissive" regime, reference is now made to FIG. 3(b). FIG. 3(b) schematically depicts a simplified example of a substrate surface. The surface includes a layer 330 of opaque material having another layer 331 formed thereon. At certain wavelengths the layer 331 is opaque. When such an opaque layer is illuminated with a light beam, the light is for the most part scattered and diffracted by the surface. Thus, such scattering and diffraction are the predominant mechanisms generating the resultant optical signal. However, for many materials, at certain wavelengths the layer 331 is at least partially transmissive. Under such conditions, thin film optical effects can be experienced by light beams directed onto the surface. One such effect is thin film interference. Thin film interference occurs when a light beam 341 passes through the partially (or wholly) transmissive material of layer 331 and combines into beam 343 with light beam 342 reflecting off the top surface 332 of layer 331. The resulting interference is a function of number of factors. Such factors include, but are not limited to, the reflectivity of top surface 332, the reflectivity at the interface 333 between layer 330 and layer 331, absorption occurring in the layer 331 of partially reflective material, the wavelength of light used to illuminate the surface and the optical thickness of the layer 331 of partially reflective material. Of course all of these factors are influenced by the wavelength of the illuminating light. The interference can be either constructive or destructive depending upon the various factors. There can be many more layers involved, but the concept is the same. Another factor is the spread of wavelengths present—lasers have no bandwidth and a long "coherence length", so interference can be produced in relatively thick layers. In broadband light beams, the coherence length can be fairly short, thereby causing interference in thinner layers. Coherence length is defined as $\lambda^2/\Delta\lambda$. The presence of a defect can alter the normal interference by changing the thickness or material properties of the surface, the defect itself, or its surroundings.

The opacity transition wavelength is different for each material. For example, polysilicon is very opaque to light at wavelengths below about 400 nm. However, at wavelengths above 400 nm polysilicon becomes a relatively transmissive material. The optical properties of a transmissive (or partially transmissive surface) surface are different than those of an opaque surface (where scattering and diffraction behavior predominate).

As briefly discussed herein above, when a substrate is illuminated by light having wavelengths in a transmissive regime 303, thin film optical properties predominate the signal producing mechanism. As noted above, such thin film optical properties include, but are not limited to phase effects and interference effects caused by thin films. In the transmissive regime 303, the thin film optical properties result in a resultant optical signal that can resembles an oscillating waveform having peaks and valleys in light intensity that vary as the wavelength changes. Thus, in the transmissive regime 302 decreasing wavelength of the illumination source is not directly related to increased defect signal.

Returning to FIG. 3(a), the inventor has discovered that when inspecting for defects, almost all semiconductor materials demonstrate this "two-regime" wavelength dependent behavior. In practice, all that seems to differ from one material or defect to another is the wavelength of the transition region 304 (in particular, the opacity transition wavelength 202). Moreover, the inventor has discovered that this "two-regime" behavior can be exploited to achieve better defect capture rates than is possible for existing technologies.

The embodiments of the invention illuminate the substrate with a wavelength (or band of wavelengths) of light that is greater than the opacity transition wavelength and also with a wavelength (or band of wavelengths) of light that is shorter than the opacity transition wavelength. By doing so a methodology using the combined signal can be used to achieve improved defect detection. Moreover, the principles of the invention are flexible. The illumination regimes need not be combined. The inspector can choose an inspection methodology that inspects using only a wavelength (or band of wavelengths) of light that is longer than the opacity transition wavelength alone. In an alternative methodology, the inspector can choose to inspect using only at a wavelength (or band of wavelengths) of light that is shorter than the opacity transition wavelength alone. The inspector can then simply choose the inspection methodology that achieves the best defect capture ratios. Typically, the methodology obtaining the greatest signal-to-noise ratios (SNR) in the resultant optical signal is chosen as the desired inspection methodology. Using such methodologies, greater sensitivity in defect detection can be achieved. Furthermore, in accordance with the principles of the invention this sensitivity can extended to detect defects in the sub-resolution range (i.e., defects of a smaller size than the resolving power of the system).

The inventor has discovered that the nature and properties of the opaque and transmission regimes and the wavelength of the opacity transition wavelength are determined by the surface characteristics (including material properties) of the layers of the substrate being inspected. As previously indicated, the resultant optical signal from the surface when illuminated is dominated by two general phenomena. First, when the surface layers are relatively opaque to the illuminating wavelengths of light, the optical signal is dominated by the light scattering and diffraction properties of the surface. Such opacity is a function of film thickness, the k (complex refractive index) of the film. As indicated, these properties are highly wavelength dependent. For example, polysilicon is very opaque at wavelengths below about 400 nm. In contrast, at wavelengths above 400 nm polysilicon is a relatively transmissive material. Thus, the opacity transition wavelength for polysilicon is about 400 nm. As such the opacity transition wavelength defines the transition region 204. Additionally, for high-K dielectric materials (such as SiLK®, Black Diamond®, or FLARE®) generally have opacity transition regions in the range of 350-360 nm. Since the forgoing materials are particularly common in semiconductor fabrication 350 nm is a particularly attractive wavelength for use in accordance with the principles of the invention. A more detailed discussion of this attractiveness is included in later paragraphs. Also, $SiO_2$ films have an opacity transition region at about 190 nm which makes this wavelength attractive.

As explained briefly hereinabove, the "transmissive" regime is an optical bandwidth of wavelengths wherein thin film properties of the substrate predominate as the cause of the resultant optical signal. Usually, a defect signal in a transmissive regime demonstrates signal intensity curve having an oscillatory pattern of light intensity peaks and valleys that vary with the wavelength (See, for example, 303 of FIG. 3(a)). In general, this pattern is related to the constructive and destructive interference effects associated with thin film optical behavior. By way of contrast, the defect signal is dominated by diffraction and scattering effects of the substrate when illuminated with wavelengths of light chosen from the "opaque" regime. In such a defect signal is generally non-oscillatory (See, for example, 302 of FIG. 3(a)).

In general, embodiments of the invention are capable of illuminating the substrate in two different optical regimes (e.g., opaque and transmissive) and capable of detecting the resultant optical signal. Alternatively, a substrate can be illuminated by a light beam having wavelengths in the opaque regime alone. In another alternative, the substrate can be illuminated by a light beam having wavelengths in the transmission regime alone. The resultant optical signals can be integrated, compared, or otherwise processed together to achieve defect detection. Usually, the approach that yields the best inspection results (e.g., the approach that provides the strongest signal, the best SNR, or some other suitably useful parameter) is employed for inspection.

A generalized method embodiment for inspecting a surface includes at least the following operations. Illuminating the surface with light in a first wavelength range selected such that the surface is opaque to the light of the first wavelength range. In such an opaque regime a first resultant optical signal is produced that is predominated by diffractive and scattering properties of the surface. An example of such a regime is shown as 302 of FIG. 3(a). Also, the surface is illuminated with light in a second wavelength range selected such that the surface is at least partially transmissive to light in the second wavelength range. In such a transmissive regime another resultant optical signal is produced that is predominated by thin film optical properties of the surface. An example of such a regime is shown as 303 of FIG. 3(a). The resultant optical signals are detected and processed to identify defects and unwanted process variations in the surface. As discussed, the substrate can also be illuminated by light having a wavelength in the opaque regime alone to obtain inspection information. Also as discussed, the substrate can also be illuminated by light having a wavelength in the transmissive regime alone to obtain inspection information.

The above steps can be supplemented with a step of determining an appropriate opacity transition wavelength (and thereby determine appropriate opaque and transmissive regimes) for the substrate. The opaque and transmissive regimes can be identified using a number of approaches. First, a substrate can be scanned at a number of wavelengths and a transition region for the substrate can be identified. Alternatively, transmission calculations using the k values of the substrate materials as function of wavelength can be used to provide an optical picture of the wavelength dependent characteristics of a substrate (in particular to determine the opacity transition wavelength or region). Once a transition region is identified, the substrate can be illuminated at wavelength (or wavelengths) above the transition region and at wavelength (or wavelengths) below the transition region so that signal generated by thin film optical properties and by the diffraction/scattering properties can be captured. Alternatively, the substrate can be illuminated at a wavelength (or wavelengths) above the transition region or at a wavelength (or wavelengths) below the transition region, which ever produces the best detect detection results.

Figure 4A:
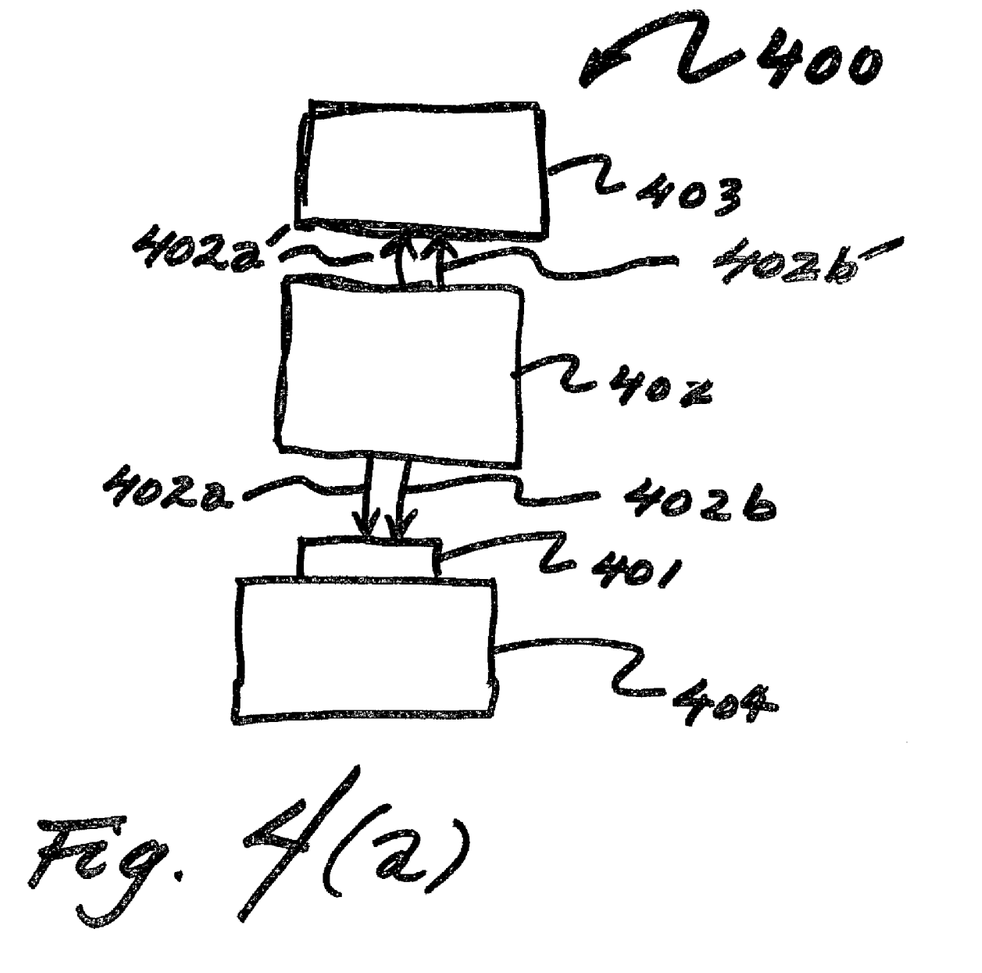
FIG. 4(a) is a simplified block depiction of a generalized inspection tool embodiment constructed in accordance with the principles of the invention.

FIG. 4(a) is a schematic block diagram illustrating an inspection tool 400 constructed in accordance with the principles of the invention. Such tools can include, without limitation, bright field type inspection tools, darkfield inspection tools, and combination bright field/darkfield inspection tools. The inventor notes that a bright field implementation is the preferred implementation. Such an apparatus includes an illumination element 402 for illuminating substrate 401. The illumination element 402 is configured so that it can illuminate the substrate 401 in two (or more) optical wavelength regimes. Typically, this is achieved by an illumination element 402 having two (or more) operative modes. A first mode is capable of illuminating the substrate 401 at a first set of wavelengths of light 402a selected for inspection of the surface in a first optical regime where the surface is opaque to the first set of wavelengths of light 402a. This first mode produces a first resultant optical signal 402a' that is predominated by diffraction and scattering of light from the substrate. Additionally, the illumination element 402 is capable of operating in a second mode that illuminates the substrate 401 at a second set of wavelengths of light 402b selected for inspection of the substrate surface in a second optical regime where the surface is at least partially transmissive to the second set of wavelengths of light 402b. This second mode produces a second resultant optical signal 402b' that is predominated by the thin film optical properties of the substrate 401. Typically, the first mode illuminates the substrate with light at wavelengths selected so that they are below an opacity transmission wavelength for the inspected substrate. Also, the second mode illuminates the substrate with light at wavelengths selected such that they are above the opacity transmission wavelength for the inspected substrate. Thus, in one preferred implementation, a first mode illuminates a substrate using wavelengths of less than about 350 nm and illuminates in a second mode with wavelengths above about 350 nm. In another preferred implementation, a first mode illuminates a substrate using wavelengths of less than about 400 nm and illuminates in a second mode with wavelengths above about 400 nm. In still another preferred implementation, a first mode illuminates a substrate using wavelengths of less than about 190 nm and illuminates in a second mode with wavelengths above about 190 nm.

The first resultant optical signal 402a' and the second resultant optical signal 402b' are received by detector system 403. The detector system 403 processes the received resultant optical signals (402a', 402b) to identify defects and/or process variations in the inspected surface. Typically the system also includes a scanning element 404 that enables the apparatus to scan the desired portions substrate. Such scanning can be achieved by a number of means known to persons having ordinary skill in the art. For example, the illuminating light can be moved over the desired portions of the surface until the substrate is scanned. Alternatively, the substrate can be moved so that the light is scanned over the desired portions of the surface thereby scanning the substrate.

In one implementation, an inspection tool 400 such as depicted in FIG. 4(a) can be operated as follows. A substrate 401 having a number of known defects is positioned in the tool. Each defect is illuminated at a variety of wavelengths to determine the optimal wavelength (or combination of wavelengths) for producing the best defect capture rate for each defect. Then the substrate is inspected at the optimal wavelength (or combination of wavelengths). In one implementation, this can be accomplished as follows.

A number of defects (of known types and sizes) on substrate 401 are illuminated using a first series of different wavelengths selected from the first set of wavelengths of light 402a in the opaque regime. For example, if the opacity transition wavelength for the substrate is determined to be 350 nm, the first series of different wavelengths (i.e., those in the opacity regime) is selected from wavelengths shorter than 350 nm. Defects can be illuminated, for example, at wavelengths of 340 nm, 330 nm, 320 nm, 310 nm, and soon. Any series of wavelengths in the opaque regime (here, wavelengths of less than 350 nm) can be chosen. The first resultant optical signals 402a' are then detected and compared to determine the optimal inspection wavelength(s) in the opaque regime. For example, wavelength(s) producing the best SNR can be used as the optimal wavelength(s).

Similarly, the defects are also illuminated using a second series of different wavelengths selected from the second set of wavelengths of light 402b in the transmissive regime. Continuing the example, for a substrate having an opacity transition wavelength of 350 nm, a second series of different wavelengths (i.e., those in the transmission regime) are selected from wavelengths longer than 350 nm. For example, the defects can be illuminated at wavelengths of 360 nm, 370 nm, 380 nm, 390 nm, and so on. Any series of wavelengths in the transmission regime (here, wavelengths of longer than 350 nm) can be chosen. The second resultant optical signals 402b' are then detected and compared to determine the optimal inspection wavelength(s) in the transmission regime. For example, wavelength(s) producing the best SNR can be used as the optimal wavelength(s).

Figure 4B:
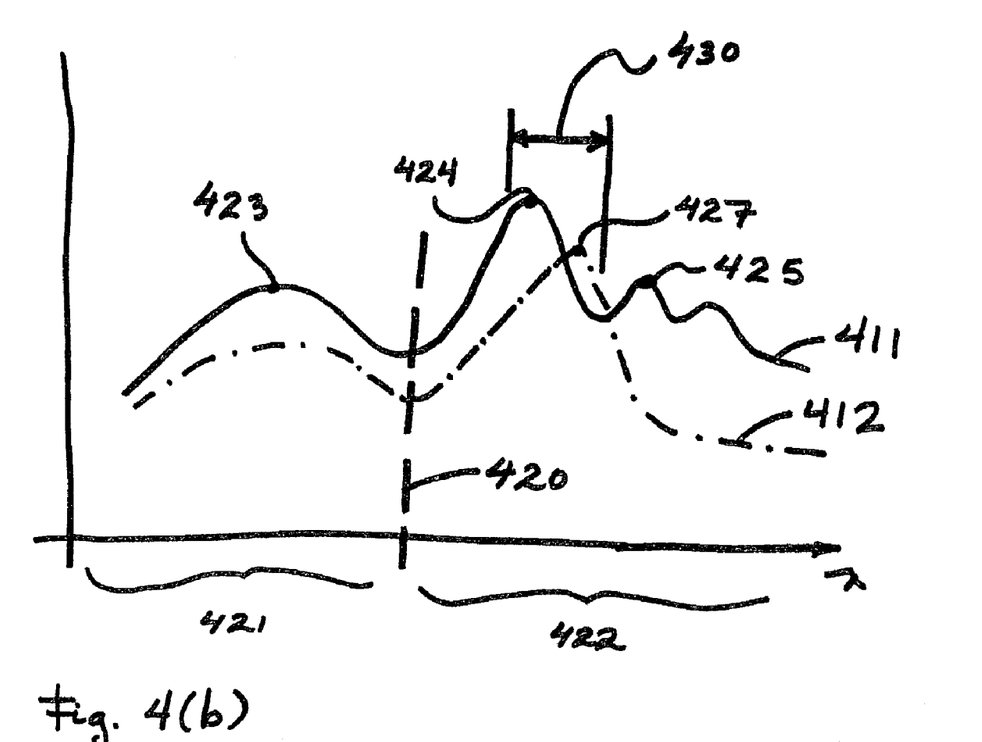
FIG. 4(b) is a simplified graphical depiction of a pair of defect signals showing an opaque regime and a transmission regime and also illustrating optimal wavelengths (or wavelength bands) for inspection in each regime.

An example of how this works can be illustrated with respect to FIG. 4(b) which graphically depicts a pair of defect signals located on a substrate 401. One defect signal 411 is for a first defect and another defect signal 412 is for a second defect. An opacity transition wavelength 420 for the relevant portions of the substrate is also depicted. Also shown are an associated opaque regime 421 and an associated transmissive regime 422.

By illuminating the surface with a series of wavelengths in the opaque regime 421, optimal wavelength(s) for detecting defect signal in the opaque regime can be then determined. For example, for the first defect this wavelength corresponds to point 423 (on the defect signal 411) where the signal caused by scattering and diffraction has the maximum SNR (and most likely the highest defect capture ratio). It should be pointed out that the optimal wavelength can correspond to a band of wavelengths.

Similarly, the defects are also illuminated using the second series of different wavelengths in the transmissive regime. The second resultant optical signals 402b' are detected and compared to determine the optimal wavelength(s) producing the best defect capture ratio in the transmission regime. Again referring to FIG. 4(b), the defect signal 411 can have a signal maxima at several different wavelengths (e.g., at points 424, 425). Thus, the amplitude of the defect signal produced by each wavelength is compared to determine the optimal wavelength in the transmissive regime 422. For example, the wavelength corresponding to point 425 of the defect signal 411 appears to offer the best SNR.

Additionally, the optimal wavelengths may be modified to capture more than one type of defect. For example, another type of defect (indicated by defect signal 412) may have a differently shaped signal curve. In the transmission regime 422 the defect signal 412 has a signal maxima at a wavelength corresponding to point 427. The process for finding the optimal inspection wavelengths proceeds as explained herein above. During such a process, it will be determined that the defect signal 412 has a signal maxima at a wavelength corresponding to point 427. In order to achieve the best capture ratio for both types of defects, a band of wavelengths in the transmission regime may provide superior defect identification. For example, a waveband 430 that encompasses the optimal wavelengths (corresponding to points 424, 427) for both types of defects can be used to maximize defect capture for both types of defects. Additionally, in some implementations, the best signal is received if the defects are illuminated with wavelengths in both regimes to obtain a composite defect signal. Thus, defects can be illuminated with wavelengths of light in the opaque regime or the transmission regime or in both regimes depending on which approach yields the best defect capture rate.

Figure 5:
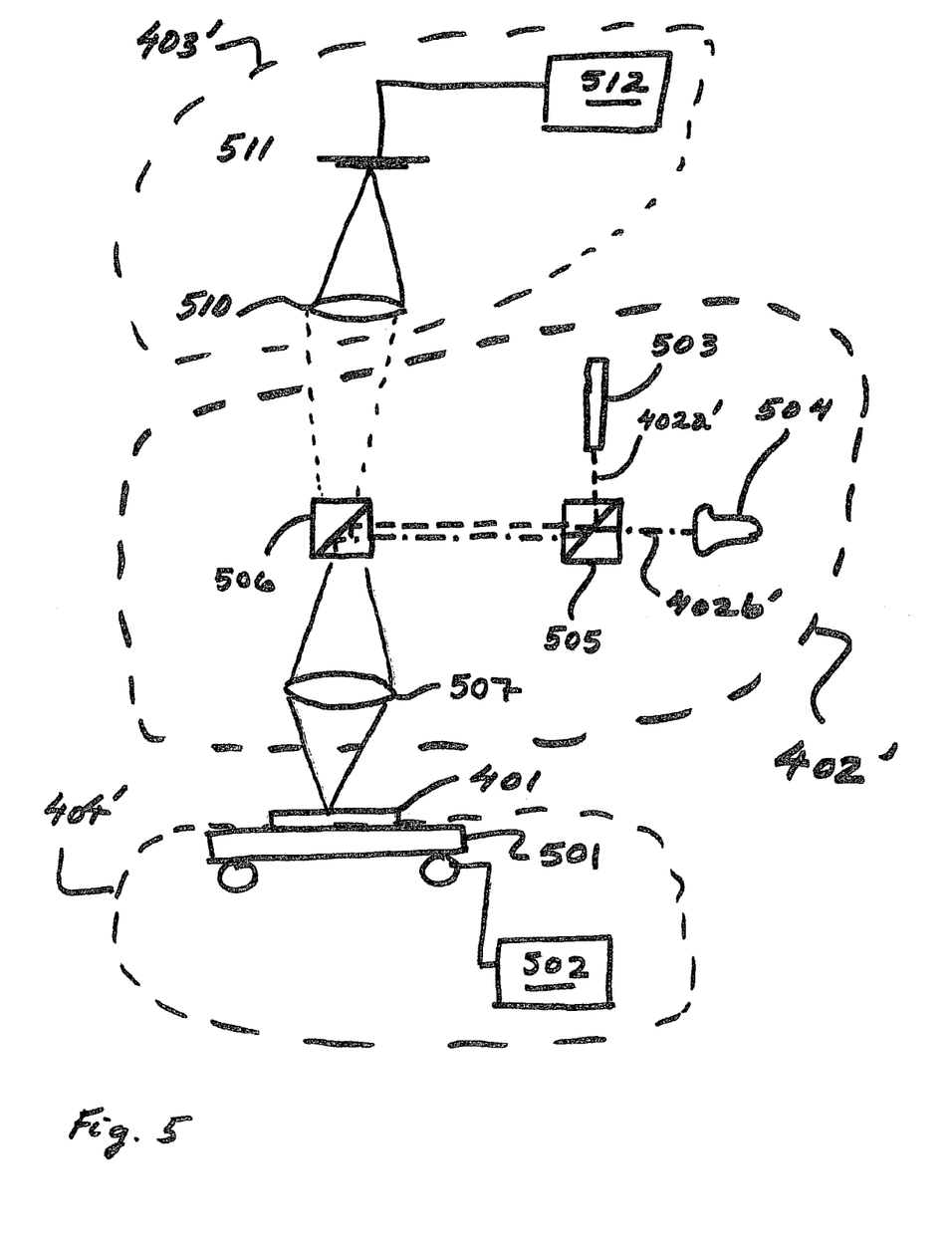
FIG. 5 is a simplified schematic depiction of an embodiment for an inspection tool embodiment constructed in accordance with the principles of the invention.

FIG. 5 is a simplified schematic depiction of one type of bright field inspection tool embodiment constructed in accordance with the principles of the invention. A substrate 401 is positioned in the tool so that it can be inspected. In the depicted embodiment, the substrate 401 is mounted on a movable stage 501 in readiness for inspection. The scanning of the stage 501 can be controlled with electronic circuitry comprising a scanning control element 502. The movable stage 501 and its control element 502 can all be included as part of a scanning element 404'. It is to be noted that the substrate 401 can be arranged on a movable stage 501 or any other type of support structure commonly used in such inspection tools. In alternative embodiments, the scanning control element 502 can be used to move other elements of the inspection tool in order to effectuate scanning of the desired portions of the substrate 401 being inspected.

With continued reference to FIG. 5, a pair of illumination sources 503 and 504 are used to generate the two operative modes of the illumination element 402'. The first illumination source 503 illuminates the substrate 401 at wavelengths below the opacity transition region and the second illumination source 504 illuminates the substrate 401 at wavelengths above the opacity transition region. As stated, the first illumination source 503 illuminates the substrate 401 at a first set of wavelengths of light (depicted by the dashed line 402a'). As previously explained, the first set of wavelengths of light operates in a first optical regime where the surface is opaque to the first set of wavelengths of light 402a'. An example of such a first illumination source 503 is a neodymium YAG laser tuned to produce an output beam of 266 nm. However, any laser capable of producing light having wavelengths of less than about 350 nm can be used. Alternatively, other lasers capable of producing light beams having wavelengths of less than about 400 nm can also be used. Also, as previously explained, a suitable first illumination source 503 is any light source capable of operating at wavelengths where the substrate produces a resultant optical signal that is predominated by diffractive and scattering properties of the substrate. Such sources include, without limitation, polychromatic sources (e.g., arc lamps) and lasers.

With continued reference to FIG. 5, a second illumination source 504 illuminates the substrate 401 at a second set of wavelengths of light (depicted by the dotted/dashed line 402a'). As previously explained, the second set of wavelengths of light operates in a second optical regime above the opacity transition region (e.g. at wavelengths where the surface is at least partially transmissive to the light 402b'). This second mode produces a second resultant optical signal 402b' that is predominated by the thin film optical properties of the substrate 401. An example of such a second illumination source 504 is a mercury xenon (Hg Xe) arc lamp which can produce a wide range of light in the visible and near UV spectrum. However, any light source capable of producing light having wavelengths of greater than about 350 nm can be used. Alternatively, in other embodiments, light sources (e.g., lasers) capable of producing light beams having wavelengths of greater than about 400 nm can also be used. Also, as previously explained, a suitable second illumination source 504 comprises any light source capable of operating at wavelengths where the substrate produces a resultant optical signal that is predominated by thin film optical properties of the substrate 401. Such sources include, without limitation, polychromatic sources (e.g., arc lamps) and lasers.

In the depicted embodiment, both the sources 503, 504 are directed onto a dichroic beam splitter 505. The dichroic beam splitter 505 is constructed such that (in this implementation) it is reflective to light having wavelengths below a certain wavelength and transmissive to wavelengths of light above a certain wavelength. In one example, the dichroic beam splitter 505 is transmissive to light having wavelengths above the opacity transition region of the substrate and reflective to light having wavelengths below the opacity transition region of the substrate. In the depicted example, the dichroic beam splitter 505 is reflective to wavelengths of light below 350 nm (e.g. 266 nm light produced by a laser source 503) and transmissive to wavelengths of light above 350 nm (e.g., a portion of the spectrum produced by an Hg Xe arc lamp source 504). Such dichroic beam splitters are well known to persons having ordinary skill in the art and available from many different manufacturers.

The light passes through the dichroic beam splitter 505 onto a second beam splitter 506 that directs a portion of the light downward toward the substrate 401 where it passes through an objective lens system 507. The objective lens system 507 corrects aberrations and focuses the light on the substrate 401 for inspection. The objective lens system 507 can comprise many different optical elements. The construction of such objective lens systems 507 are well known to those having ordinary skill in the art and therefore will not be described in detail here. Because lens systems capable of operating over large bandwidths of wavelengths are somewhat difficult to design and fabricate, separate optical components can be implemented for each waveband in order to obtain good optical image quality. For example, a separate narrow band objective lens and associated lenses can be used for operation with a laser operating at a wavelength of 266 nm. A second, wide band objective lens and associated lenses can be implemented for use above 360 nm where a Hg or HgXe lamp operates as the illumination source. For example, in such an implementation, an Hg lamp can be filtered to used only g-line (404 nm) and/or i-line (436 nm) light in regions where polysilicon is optically transmissive.

Light directed onto the substrate 401 produces resultant optical signal which passes back through the objective lens systems 507 and second beam splitter 506 and into a detector system 403'. As explained with respect to FIG. 4, the resultant optical signal includes a first and second resultant optical signal (402a', 402b') (as shown in FIG. 4) which are received by detector system 403'. The depicted detector system 403' includes a focusing element 510 that receives the resultant optical signal and focuses the received resultant optical signal onto a detector element 511. The focusing element 510 typically includes many optical elements that can be used to adjust the magnification, focus, aberration correction, resolution, and other optical properties of the system in order to enhance the tools inspection characteristics. The construction of such focusing elements is well known to persons having ordinary skill in the art.

After the resultant optical signal passes through the focusing element 510 it is received by a detector element 511. The detector element 511 can comprise a wide range of photosensitive detector devices. Such devices include, without limitation, TDI (time delay integration) devices, CCD (charge coupled devices), photodiodes, PMT (photo multiplier tubes), as well as a wide range of related devices. The inventor also particularly contemplates that the depicted detector element 511 includes array type photosensitive detector devices. In one implementation, a preferred detector element 511 comprises a backside thinned TDI sensor array. Such arrays are available from many different manufacturers (e.g., from Hamamatsu Photonic KK of Hamamatsu Japan). Such a detector element 511 receives the resultant optical signal and transmits the signal as either electronic or optical information to image processing circuitry 512 for analysis. The image processing circuitry uses various image processing techniques and algorithms to analyze the resultant optical signal to identify defects. Such image processing circuitry 512 can include microprocessors, PLD's, ASIC's, DSP's, as well as wide range of other digital or analog electronic devices known to persons having ordinary skill in the art.

Figure 6:
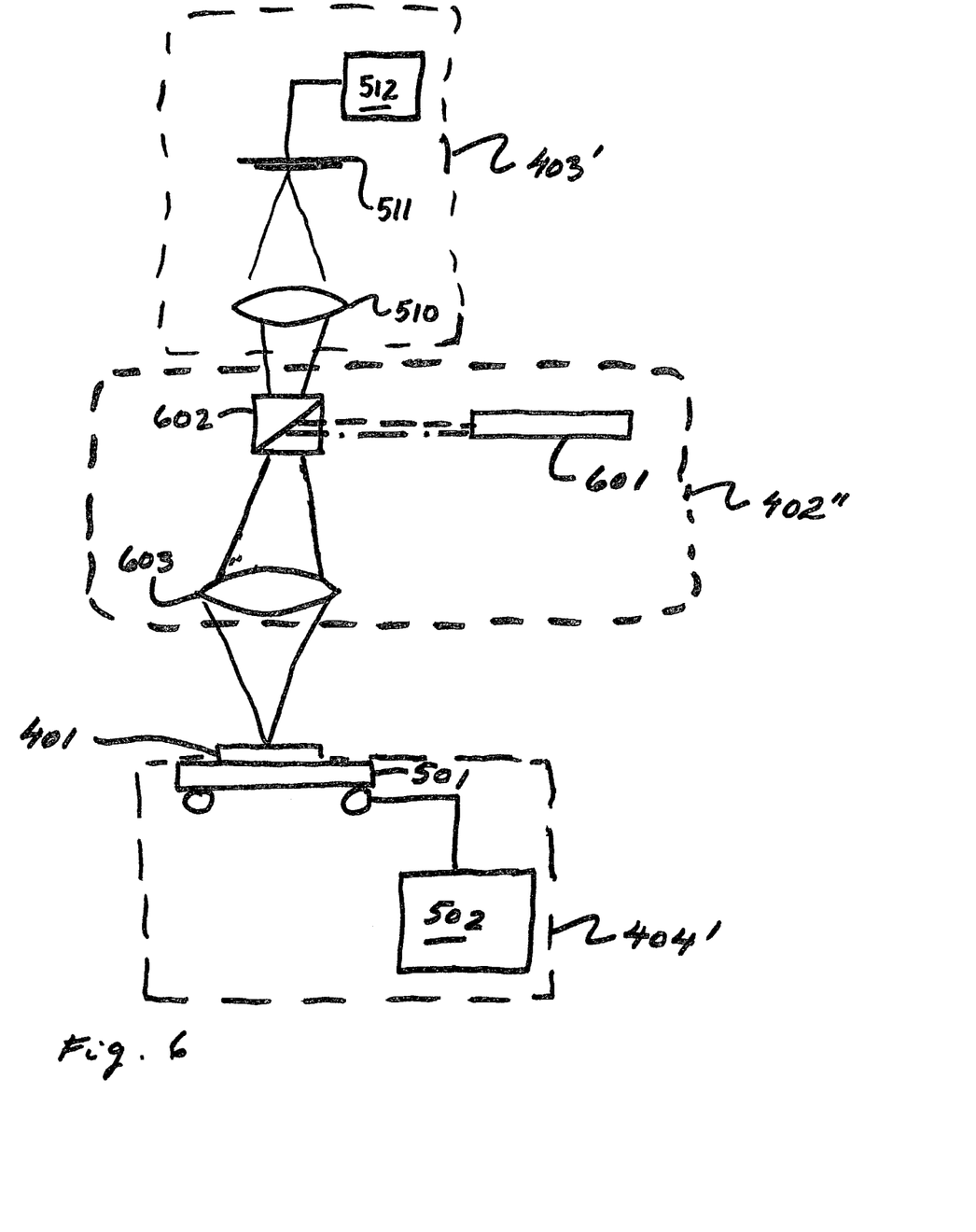
FIG. 6 is a simplified schematic depiction of another embodiment for an inspection tool embodiment constructed in accordance with the principles of the invention.

Another implementation is depicted in FIG. 6. The depicted embodiment is somewhat similar to the embodiment shown in FIG. 5. As with the embodiment of FIG. 5, the substrate 401 is positioned in the tool so that it can be inspected. As with the embodiment of FIG. 5, the substrate 401 is mounted on a movable stage 501 so that scanning can be controlled with electronic circuitry 502. The movable stage 501 and its controlling electronic circuitry 502 can all be included as part of a scanning element 404'.

One significant difference in the depicted embodiment is the configuration of the illumination element 402". Instead of the pair of illumination sources 503 and 504 used in FIG. 5, a single illumination device 601 is used. In the depicted embodiment, a single illumination device 601 is used to generate the two operative modes of the illumination element 402". Typically (but not exclusively), the illumination device 601 is a multi-wavelength laser device. In a first mode the device 601 illuminates the substrate 401 at wavelengths below the opacity transition region and in a second mode illuminates the substrate 401 at wavelengths above the opacity transition region. As stated previously herein, the first mode illuminates the substrate 401 at a first set of wavelengths of light (depicted by the dashed line) that operates in a first optical regime where the surface is opaque to the first set of wavelengths of light. In the second mode of operation the illumination device 601 illuminates the substrate 401 at a second set of wavelengths of light (depicted by the dotted/dashed line) in a second optical regime where the thin film optical properties of the substrate predominate.

An example of such an illumination device 601 is a neodymium YAG laser. In the first mode the laser can be tuned to produce an output beam of 266 nm (i.e., the $4^{th}$ harmonic of the laser). Additionally, the illumination device 601 can be tuned to produce an output beam of 532 nm (i.e., the $2^{nd}$ harmonic of the laser). Thus, the illumination device 601 can be tuned to illuminate the substrate 401 at a first set of wavelengths of light (depicted by the dashed line) and at a second set of wavelengths of light (depicted by the dotted/dashed line). As previously explained, the first set of wavelengths of light operate in a first optical regime (e.g. at wavelengths where the surface is relatively opaque to the light and the second set of wavelengths of light operate in a second optical regime (e.g. at wavelengths where the surface is at least partially transmissive to the light). As previously explained, the first mode produces a first resultant optical signal that is predominated by the diffraction and scattering optical properties of the substrate 401 and the second mode produces a second resultant optical signal that is predominated by the thin film optical properties of the substrate 401. If a neodymium YAG laser is implemented as the illumination device 601, it can be tuned to produce an output beam at both 266 nm and 532 nm simultaneously. Thus, such an illumination device 601 can be used to produce wavelengths of light both above and below 350 nm to satisfy both modes of operation. Alternatively, for some other substrates, the illumination device 601 can be used to produce wavelengths of light both above and below 400 nm to satisfy both modes of operation. Using yet other devices 601, other opacity transition region wavelengths can be accommodated. Additionally, some types of polychromatic sources can be used (with appropriate filters) to accommodate such single source dual-mode operation.

The light produced in both modes is directed onto a beam splitter 602 which directs the light through an objective lens system 603 onto a desired portion of the substrate 401. The beam splitter 602 and objective lens system 603 are essentially the same systems as discussed hereinabove with respect to FIG. 5 and so will not be described in detail here.

Light directed onto the substrate 401 produces resultant optical signal which passes back through the objective lens systems 603 and beam splitter 602 and into a detector system 403'. As previously explained, the resultant optical signal is received by detector system 403' where it can be processed to detect defects or other surface charateristics. The depicted detector system 403' includes a focusing element 510 that receives the resultant optical signal and focuses the received resultant optical signal onto a detector element 511. Such a focusing element 510 and detector element 511 are as described previously (e.g., with respect to FIG. 5) and therefore will not be discussed here. The detector element 511 receives the resultant optical signal and transmits the signal as either electronic or optical information to image processing circuitry 512 for analysis. As with the image processing circuitry of the embodiment shown in FIG. 5, the image processing circuitry 512 uses various image processing techniques and algorithms to analyze the resultant optical signal to identify defects.

Figure 7:
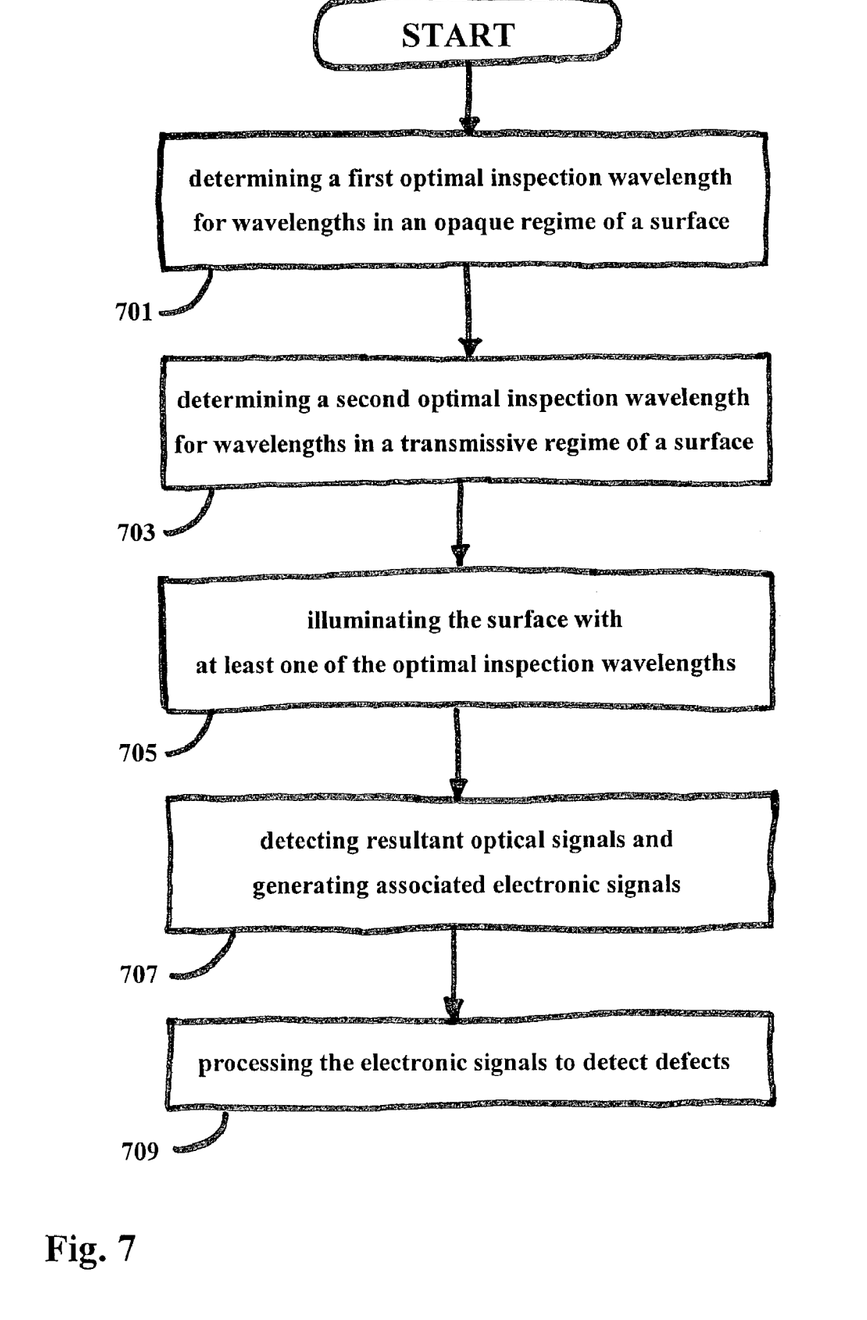
FIG. 7 is a flow diagram illustrating one embodiment of a process for inspecting a surface of substrate in accordance with the principles of the present invention.

The above-described embodiments can implement methods for increasing the sensitivity an SNR of surface inspection techniques. FIG. 7 is a flow diagram illustrating one method of detecting defects in accordance with the principles of the invention.

The method includes determining a first optimal inspection wavelength (or waveband of many wavelengths) chosen from a first wavelength range selected such that the surface is opaque to the light of the first wavelength range (i.e., in the opaque regime), thereby producing a resultant optical signal that is predominated by diffractive and scattering properties of the surface (Step 701). As described hereinabove, this is typically achieved by illuminating a substrate defect(s) at several different wavelengths of light such that each of the wavelengths are shorter than the opacity transition wavelength for the substrate. The resultant optical signals are then compared to determine a first optimal wavelength (or wavelength band) that exhibits the best defect capture rate in the opaque regime. This determination can be based on a number of factors including, but not limited to, SNR and signal intensity.

The method includes determining a second optimal inspection wavelength (or waveband of many wavelengths) chosen from a second wavelength range selected such that the surface is at least partially transmissive to the light of the first wavelength range (i.e., in the transmissive regime), thereby producing a resultant optical signal that is predominated by thin film optical properties (e.g., thin film interference effects, etc.) of the surface (Step 703). As described hereinabove, this is typically achieved by illuminating a substrate defect(s) at several different wavelengths of light such that each of the wavelengths are longer than the opacity transition wavelength for the substrate. The resultant optical signals are then compared to determine a second optimal wavelength (or wavelength band) that exhibits the best defect capture rate in the transmissive regime. This determination can be based on a number of factors including, but not limited to, SNR and signal intensity.

Once optimal wavelengths (or bands of wavelengths) have been determined for the opaque and transmissive regimes the surface is illuminated using selected wavelengths (or bands of wavelengths) (Step 705). It should be specifically noted that the illumination can be conducted in accordance with several schemes. The illumination can be conducted at the first optimal wavelength (or band of wavelengths) determined for wavelengths in the opaque regime. Alternatively, the illumination can be conducted at the second optimal wavelength (or band of wavelengths) determined for wavelengths in the transmissive regime. In still another approach, the illumination can be conducted at both the first optimal wavelength (or band of wavelengths) and the second optimal wavelength (or band of wavelengths) to obtain a combined defect signal generated by simultaneous illumination in both regimes. Although, simultaneous illumination is preferred, sequential illumination schemes can also be used. Generally, speaking the selected illumination wavelength(s) are selected because they yield the best defect capture ratio. Generally, it is not known beforehand whether inspection in both regimes, or inspection in one regime or the other will yield the best defect capture ratio. In a optional step, a process of comparing the three indicated approaches can be conducted to find the best approach which can then be applied to a full inspection. Typically, the capture ratio is highest for resultant signals having the highest SNR.

Once illuminated, the resultant optical signals which result from said illumination of the substrate are detected and used to generate associated electronic signals (Step 707). The electronic signal is then processed to detect defects and process variations in the substrate (Step 709). A number of signal processing methods known to persons having ordinary skill in the art can be implemented with the present methodologies to obtain defect detection in accordance with the principles of the invention. Inspection in accordance with the principles of the invention can be performed after each process step in a semiconductor fabrication process.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. In particular, it is contemplated by the inventors that embodiments using a wide range of lasers, polychromatic sources (e.g., arc lamps), and other illumination devices are within the scope of this patent. Moreover, the inventor contemplates that the principles of the present invention can be practiced with substrates have a wide range of opacity transition wavelengths. Further, reference in the claims to an element in the singular is not intended to mean "one and only one" unless explicitly stated, but rather, "one or more". Furthermore, the embodiments illustratively disclosed herein can be practiced without any element which is not specifically disclosed herein.

I claim:

1. A method of inspecting a surface, the method comprising:

providing a substrate characterized by an opacity transition wavelength configured such that when the surface is illuminated with wavelengths of light in an opaque regime of light having wavelengths shorter than the opacity transition wavelength a first resultant optical signal is produced that is predominated by diffractive and scattering properties of the surface and configured such that when the surface is illuminated with wavelengths of light in a transmissive regime of light having wavelengths longer than the opacity transition wavelength a second resultant optical signal is produced that is predominated by thin film optical properties of the surface;

determining a first optimal inspection wavelength band selected from the wavelengths in the opaque regime defined by the wavelengths shorter than the opacity transition wavelength of the substrate such that the first optimal inspection wavelength band is optimal for detecting a defect on the substrate;

determining a second optimal inspection wavelength band selected from the wavelengths in the transmissive regime defined by the wavelengths longer than the opacity transition wavelength of the substrate such that the second optimal inspection wavelength band is optimal for detecting the defect on the substrate;

illuminating the substrate with light in the first and second optimal inspection wavelength bands, wherein the light in the second optimal inspection wavelength band comprises light having a band of wavelengths;

detecting the first and second resultant optical signals produced by the illumination and generating associated electronic signals; and processing the electronic signals using a non-defect signal to detect defects and process variations in the surface.

2. The method of claim 1, wherein the first optimal inspection wavelength band comprises one of a single wavelength selected from the wavelengths in the opaque regime and a band of wavelengths selected from the wavelengths in the opaque regime.

3. The method of claim 1, wherein said illuminating comprises simultaneously illuminating the substrate using the light in the first optimal inspection wavelength band and using the light in the second optimal inspection wavelength band.

4. The method of claim 1, wherein said illuminating comprises sequentially illuminating the substrate using the light in the first optimal inspection wavelength band and the light in the second optimal inspection wavelength band.

5. The method of claim 1, wherein the opacity transition wavelength is at about 350 nm.

6. A method of inspecting a surface, the method comprising:
a) illuminating the surface with:
   i) light in a first wavelength range selected such that the surface is opaque to the light of the first wavelength range, thereby producing a first resultant optical signal that is predominated by diffractive and scattering properties of the surface, wherein the light in the first wavelength range is further selected such that the light in the first wavelength range is optimal for detecting a defect on the surface; and
   ii) light in a second wavelength range selected such that the surface is at least partially transmissive to the light in the second wavelength range, thereby producing a second resultant optical signal that is predominated by thin film optical properties of the surface, wherein the light in the second wavelength range is further selected such that the light in the second wavelength range is optimal for detecting the defect on the surface, and wherein the light in the second wavelength range comprises light having a band of wavelengths;
b) detecting the first and second resultant optical signals and generating associated electronic signals; and
c) processing the electronic signals using a non-defect signal to detect defects and process variations in the surface.

7. The method of claim 6, wherein said illuminating comprises illuminating the surface with light having wavelengths less than about 350 nm and light having wavelengths greater than about 350 nm.

8. The method of claim 6, wherein said illuminating comprises illuminating the surface with light having wavelengths less than about 400 nm and light having wavelengths greater than about 400 nm.

9. The method of claim 6, wherein said illuminating the surface with the light in the first wavelength range is accomplished using a first laser.

10. The method of claim 9, wherein said illuminating the surface with the light in the second wavelength range is accomplished with at least one of a polychromatic source and a second laser.

11. The method of claim 6, wherein said illuminating the surface with the light in the first wavelength range is accomplished using a first polychromatic light source.

12. The method of claim 11, wherein said illuminating the surface with the light in the second wavelength range is accomplished with a second polychromatic source.

13. The method of claim 11, wherein said illuminating the surface with the light in the second wavelength range is accomplished using the first polychromatic light source.

14. The method of claim 6, wherein said illuminating, said detecting, and said processing are accomplished in accordance with a bright field defect detection methodology.

15. The method of claim 6, wherein said illuminating, said detecting, and said processing are accomplished in accordance with a darkfield defect detection methodology.

16. The method of claim 6, wherein said illuminating, said detecting, and said processing are accomplished in accordance with bright field and darkfield defect detection methodologies.

17. An apparatus for detecting defects in an inspected surface, the apparatus comprising:
an illumination element for illuminating a surface, the illumination element having two operative modes,
   a first mode for producing first wavelengths of light selected for inspection of the surface in a first optical regime where the surface is opaque to the first wavelengths of light, thereby producing a first resultant optical signal that is predominated by diffractive and scattering properties of the surface, wherein the first wavelengths of light are further selected such that the first wavelengths of light are optimal for detecting a defect on the surface; and
   a second mode for producing second wavelengths of light selected for inspection of the surface in a second optical regime where the surface is at least partially transmissive to the second wavelengths of light, thereby producing a second resultant optical signal that is predominated by thin film optical properties of the surface, wherein the second wavelengths of light are further selected such that the second wavelengths of light are optimal for detecting the defect on the surface, and wherein the light of the second wavelengths comprises light having a band of wavelengths;
an optical system for receiving the first and second resultant optical signals from the inspected surface and producing associated electronic signals;
a scanning element that enables the apparatus to scan desired portions of the inspected surface; and
electronic circuitry for processing the electronic signals using a non-defect signal to detect defects and process variations in the inspected surface.

18. The apparatus of claim 17, wherein the apparatus is configured as one of a bright field inspection tool and a darkfield inspection tool.

19. The apparatus of claim 17, wherein the first wavelengths of light comprise a first bandwidth of light.

20. The apparatus of claim 19, wherein the illumination element includes a laser capable of producing the first wavelengths of light.

21. The apparatus of claim 20, wherein the laser produces a first peak light intensity at a wavelength of about 266 nm and a second peak light intensity at a wavelength of about 532 nm.

22. The apparatus of claim 19, wherein the illumination element includes a polychromatic light source for producing the second wavelengths of light.

23. The apparatus of claim 19, wherein the first wavelengths of light comprise wavelengths below about 350 nm, and wherein the second wavelengths of light comprise wavelengths above about 350 nm.

24. The apparatus of claim 23, wherein the first wavelengths of light are produced by a laser, and wherein the second wavelengths of light are produced by a polychromatic light source.

25. The apparatus of claim 24, wherein the polychromatic light source comprises an arc lamp.

26. The apparatus of claim 17, wherein the optical system includes a photo detector for receiving the first and second resultant optical signals from the inspected surface and producing the associated electronic signals.

27. The apparatus of claim 26, wherein the photo detector includes a backside thinned time delay integration photo sensor.

28. The apparatus of claim 17, wherein the electronic circuitry comprises an image processor.

* * * * *